United States Patent
Silverstein

(10) Patent No.: US 6,443,930 B1
(45) Date of Patent: Sep. 3, 2002

(54) MALE INCONTINENT GARMENT

(76) Inventor: Joseph Silverstein, 66-12 102nd St., Apt. 6-E, Rego Park, NY (US) 11374

( * ) Notice: Subject to any disclaimer, the term of this patent is extended or adjusted under 35 U.S.C. 154(b) by 0 days.

(21) Appl. No.: 09/950,298

(22) Filed: Sep. 10, 2001

(51) Int. Cl.[7] .................................................. A61F 13/15
(52) U.S. Cl. ..................................... 604/353; 604/349
(58) Field of Search ................. 604/346–649, 604/351, 353, 385.09, 11

(56) References Cited

U.S. PATENT DOCUMENTS

| | | | | |
|---|---|---|---|---|
| 2,439,683 A | | 4/1948 | Broderick | 128/295 |
| 2,920,625 A | * | 1/1960 | Green | 128/283 |
| 3,447,536 A | * | 6/1969 | Snyder | 128/283 |
| 3,489,150 A | * | 1/1970 | Glaude | 128/295 |
| 4,387,726 A | * | 6/1983 | Denard | 128/760 |
| 4,813,943 A | | 3/1989 | Smith | 604/329 |
| 4,886,510 A | * | 12/1989 | Matsuura | 604/353 |
| 5,346,483 A | * | 9/1994 | Thaxton, Sr. | 604/353 |
| 5,593,389 A | * | 1/1997 | Chang | 604/174 |
| 5,618,277 A | * | 4/1997 | Goulter | 604/349 |
| 5,618,279 A | * | 4/1997 | Pudlo | 604/385.1 |
| 5,716,350 A | * | 2/1998 | Ryan | 604/385.1 |
| 5,735,837 A | | 4/1998 | Ishikawa | 604/385.1 |
| 5,797,890 A | * | 8/1998 | Goulter et al. | 604/351 |
| 5,810,799 A | * | 9/1998 | Slater | 604/385.1 |
| 5,984,910 A | | 11/1999 | Berke | 604/352 |
| 6,010,489 A | * | 1/2000 | Blackburn | 604/353 |
| 6,129,718 A | | 10/2000 | Wada | 604/378 |
| 6,197,011 B1 | | 3/2001 | Freitas et al. | 604/385.03 |

FOREIGN PATENT DOCUMENTS

GB 2 106 395 A * 4/1983 ............. A61F/5/44

* cited by examiner

Primary Examiner—Glenn K. Dawson
Assistant Examiner—Michael Bogart
(74) Attorney, Agent, or Firm—Richard L. Miller

(57) ABSTRACT

A male incontinent garment that includes a waistband, a crotch band, and a pouch. The crotch band has an anterior portion with an posterior surface. The pouch is a sheet of material that is folded unto itself to form a tube. The tube has an interior surface, an exterior surface with an anterior portion, and is vertically-oriented and open ended for receiving and holding the penis in an up position and a down position depending upon user preference. The interior surface of the tube is lined with an absorbent material, while the anterior portion of the exterior surface of the tube has hooks of hook and loop fasteners thereon that cooperate with the posterior surface of the anterior portion of the crotch band which is not only of a material that is absorbent but is also of one that is cooperative with hooks of hook and loop fasteners.

10 Claims, 1 Drawing Sheet

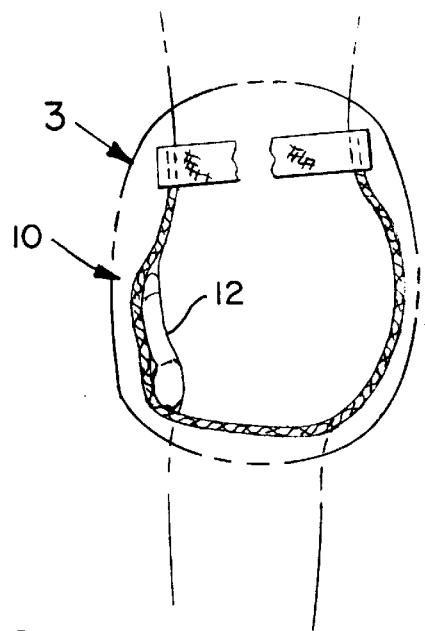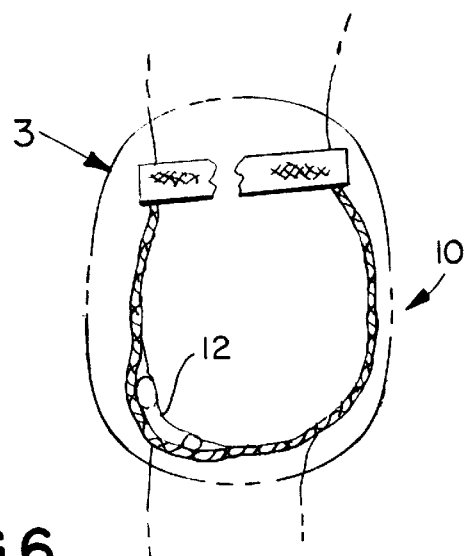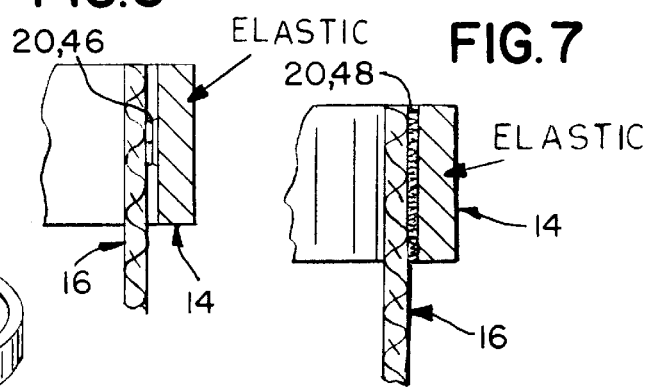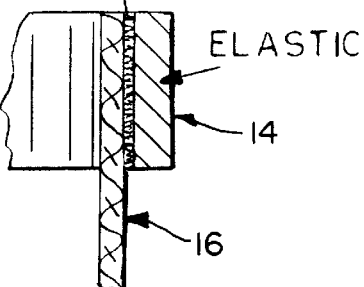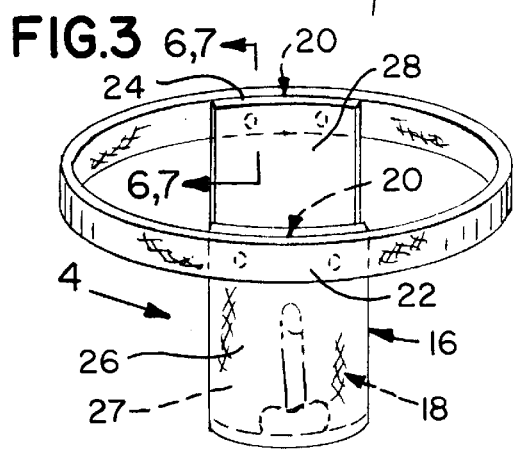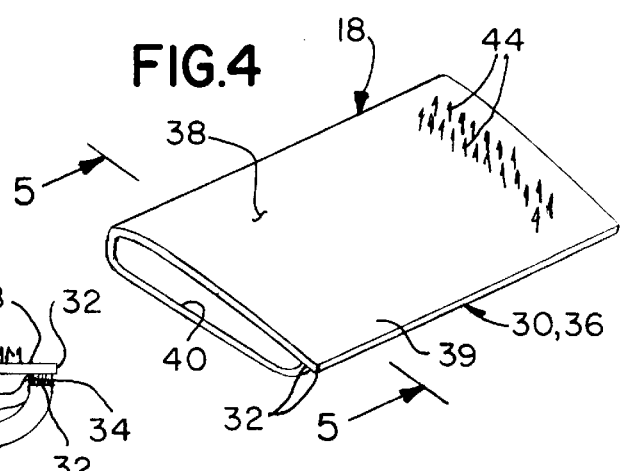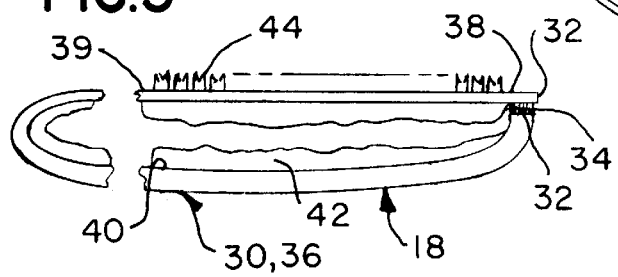

MALE INCONTINENT GARMENT

BACKGROUND OF THE INVENTION

1. Field of the Invention

The present invention relates to an incontinent garment. More particularly, the present invention relates to a male incontinent garment.

2. Description of the Prior Art

Numerous innovations for male incontinent devices have been provided in the prior art that will be described. Even though these innovations may be suitable for the specific individual purposes to which they address, however, they differ from the present invention.

A FIRST EXAMPLE, U.S. Pat. No. 2,439,683 to Broderick teaches a sanitary receptacle comprising a body-encircling belt, an outer flexible waterproof bag connected to and depending from said belt, and an inner flexible bag within said waterproof bag arranged to receive liquid-absorbing material, said inner bag having an organ-receiving aperture in the inner wall thereof, one of said bags having its opposite side edges open, and separable fasteners disposed between said open edges for releasably closing said open edges.

A SECOND EXAMPLE, U.S. Pat. No. 4,813,943 to Smith teaches a wearable urinary incontinence collector. It consists of a pair of bags designed and shaped to be worn on the inside thighs of an individual appropriately strapped to the legs. A frontal web covers the groin area and supports the bags in connection with a suitable array of straps. The arrangement is virtually leak-proof and inconspicuous when worn while standing, sitting, or lying.

A THIRD EXAMPLE, U.S. Pat. No. 5,735,837 to Ishikawa teaches a urine-absorbent bag for incontinence having a surrounding wall and an upper peripheral edge defining an opening for insertion of the wearer's penis, the surrounding wall being provided with a cut extending from the upper peripheral edge of the opening toward a bottom edge of the bag so as to divide an upper portion in two, an elastic sheet being attached to the surrounding wall over a region extending in the proximity of the cut.

A FOURTH EXAMPLE, U.S. Pat. No. 5,984,910 to Berke teaches an urinary incontinence device for use by a male that includes an undergarment worn closely to the body and including an opening or hole through which the penis passes and is kept upright and close to the body by a flap across the opener in the undergarment. The flap may include an occlusion device integrally incorporated therein and aligned with the opening to be positioned between the base of the shaft of the penis and the scrotum to occlude the urethral passage of the penis. The occlusion device is designed to apply sufficient pressure to occlude the urethral passage without cutting off circulation of blood within the penis through the dorsal vein. The flap design maintains and retains an optimum position of the penis and occlusion of the urethral passage to prevent urine discharge in a form fitting undergarment that allows significant freedom of movement by the wearer. The occlusion device has alternative embodiments where there is no integral undergarment, such as a bands and stretchable wraps that include the occlusion device. One alternative embodiment includes an occlusion device having an adjustably expandable chamber and pump. A method for using the urinary incontinence device of the present invention is also disclosed.

A FIFTH EXAMPLE, U.S. Pat. No. 6,129,718 to Wada teaches a urine-receiving pad for men including a bag of a laminated sheet which includes an inner sheet, an outer sheet and an absorbent core therebetween, and a pair of elastic members provided along the opening. By holding and pushing both ends of the elastic members with fingers, the elastic members are buckling-deformed to open the opening. When a penis is inserted into the opening and then the fingers are released, the penis is suitably pressed by elastic restoration forces of the elastic members, to prevent easy coming out of the penis therefrom. Since the pressing force resulting from the buckling-deformation of the elastic members is so small, too much pressure onto the penis is prevented. Further, the urine-receiving pad can be attached with only one hand.

A SIXTH EXAMPLE, U.S. Pat. No. 6,197,011 B1 to Wada teaches a male incontinence diaper for absorbing urine from a male user. The male incontinence diaper includes a back panel with a hole therethrough extending between the front and back faces of the back panel. A front flap is coupled to back panel along the side edges and the bottom edge of the back panel to cover the hole of the back panel. An elongate flexible belt strap is coupled to the back panel adjacent the top edge of the back panel.

It is apparent that numerous innovations for male incontinent devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a male incontinent garment that avoids the disadvantages of the prior art.

ANOTHER OBJECT of the present invention is to provide a male incontinent garment that is simple and inexpensive to manufacture.

STILL ANOTHER OBJECT of the present invention is to provide a male incontinent garment that is simple to use.

BRIEFLY STATED, STILL YET ANOTHER OBJECT of the present invention is to provide a male incontinent garment that includes a waistband, a crotch band, and a pouch. The crotch band has an anterior portion with an posterior surface. The pouch is a sheet of material that is folded unto itself to form a tube. The tube has an interior surface, an exterior surface with an anterior portion, and is vertically-oriented and open ended for receiving and holding the penis in an up position and a down position depending upon user preference. The interior surface of the tube is lined with an absorbent material, while the anterior portion of the exterior surface of the tube has hooks of hook and loop fasteners thereon that cooperate with the posterior surface of the anterior portion of the crotch band which is not only of a material that is absorbent but is also of one that is cooperative with hooks of hook and loop fasteners.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

DESCRIPTION OF THE DRAWING

The figures of the drawing are briefly described as follows:

FIG. 1 is a diagrammatic side elevational view, in partial section, of the present invention in use holding the penis in an up position;

FIG. 2 is a diagrammatic side elevational view, in partial section, of the present invention in use holding the penis in a down position;

FIG. 3 is an enlarged diagrammatic perspective view of the area generally enclosed by the dotted curves identified by arrows 3 in FIGS. 1 and 2 of the present invention;

FIG. 4 is an enlarged diagrammatic perspective view taken generally in the direction of arrow 4 in FIG. 3 of the pouch of the present invention;

FIG. 5 is an enlarged diagrammatic cross sectional view taken along line 5—5 in FIG. 4.

FIG. 6 is an enlarged diagrammatic cross sectional view taken along line 6—6 in FIG. 3 of a first apparatus for attaching the crotch band of the present invention to the waist band of the present invention; and FIG. 7 is an enlarged diagrammatic cross sectional view taken along line 5—5 in FIG. 3 of a second apparatus for attaching the crotch band of the present invention to the waist band of the present invention.

LIST OF REFERENCE NUMERALS UTILIZED IN THE DRAWING 10 male incontinent garment of present invention for holding penis 12 in one of up position and down position
12 penis
14 waistband
16 crotch band for suspending between legs of user
18 pouch for receiving penis 12
20 apparatus for attaching crotch band 16 to waistband 14
22 anterior portion of waistband 14
24 posterior potion of waistband 14
26 anterior portion of crotch band 16
27 posterior surface of anterior portion 26 of crotch band 16
28 posterior portion of crotch band 16
30 sheet of material of pouch 18
32 pair of opposite edges of sheet of material 30 of pouch 18
34 hook and loop fasteners attaching pair of opposite edges 32 of sheet of material 30 of pouch 18 to each other to form tube 36 of pouch 18
36 tube of pouch 18 for receiving penis 12 and holding penis 12 in an up position and a down position depending upon user preference
38 exterior surface of tube 36 of pouch 18
39 anterior portion of exterior surface 38 of tube 36 of pouch 18
40 interior surface of tube 36 of pouch 18
42 absorbent material lining interior surface 40 of tube 36 of pouch 18
44 hooks of hook and loop fasteners on anterior portion 39 of exterior surface 38 of tube 36 of pouch 18
46 snaps of apparatus 20
48 hook and loop fasteners of apparatus 20

DESCRIPTION OF THE PREFERRED EMBODIMENT

Referring now to the figures, in which like numerals indicate like parts, and particularly to FIGS. 1 and 2, the male incontinent garment of the present invention is shown generally at 10 for holding a penis 12 in an up position and in a down position, respectively.

The general configuration of the male incontinent garment 10 can best be seen in FIG. 3, and as such, will be discussed with reference thereto.

The male incontinent garment 10 comprises a waistband 14, a crotch band 16 that is suspended from the waistband 14, a pouch 18 that is attached to the crotch band 16 and is for receiving the penis 12, and apparatus 20 for attaching the crotch band 16 to the waistband 14.

The specific configuration of the waistband 14 and the crotch band 16 can best be seen in FIG. 3, and as such, will be discussed with reference thereto.

The waistband 14 is slender, elongated, endless, elastic, and has an anterior portion 22 and an posterior potion 24.

The crotch band 16 is for suspending between the legs of a user, and is flat, elongated, and has an anterior portion 26 that is replaceably attached to the anterior portion 22 of the waistband 14 and has a posterior surface 27 that is absorbent so as to allow the garment 10 to be used without the pouch 18 if so desired, and a posterior portion 28 that is replaceable attached to the posterior portion 26 of the waistband 14.

The specific configuration of the pouch 18 can best be seen in FIGS. 4 and 5, and as such, will be discussed with reference thereto.

The pouch 18 is replaceably attached to the posterior surface 27 of the anterior portion 26 of the crotch band 18.

The pouch 18 is a sheet of material 30 that has a pair of opposite edges 32.

The sheet of material 30 is folded unto itself and the pair of opposite edges 32 thereof are attached to each other by hook and loop fasteners 34 so as to form a tube 36 that is vertically-oriented and open ended for receiving the penis 12 and holding the penis 12 in an up position and a down position depending upon user preference.

The tube 36 has an exterior surface 38 with an anterior portion 39, and an interior surface 40.

The interior surface 40 of the tube 36 is lined with an absorbent material 42, while the anterior portion 39 of the exterior surface 38 of the tube 36 has hooks 44 of hook and loop fasteners thereon that cooperate with the posterior surface 27 of the anterior portion 26 of the crotch band 16 which is not only of a material that is absorbent, but is also of one that is cooperative with hooks of hook and loop fasteners.

The specific configuration of the apparatus 20 can best be seen in FIGS. 6 and 7, and as such, will be discussed with reference thereto.

As shown in FIG. 6, the apparatus 20 is snaps 46.

As shown in FIG. 7, the apparatus 20 is hook and loop fasteners 48.

It will be understood that each of the elements described above, or two or more together, may also find a useful application in other types of constructions differing from the types described above.

While the invention has been illustrated and described as embodied in a male incontinent garment, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. A male incontinent garment, comprising:

a) a waistband;

b) a crotch band;

c) a pouch; and d) means for attaching said crotch band to said waistband, wherein said crotch band is suspended from said waistband;

wherein said pouch is attached to said crotch band; and

Wherein said pouch is for receiving the penis, wherein said waistband is slender;

wherein said waistband is elongated;

wherein said waistband is endless;

wherein said waistband is elastic;

wherein said waistband has an anterior portion; and wherein said waistband has an posterior potion, wherein said crotch band has an anterior portion;

wherein said anterior portion of said crotch band is replaceable attached to said anterior portion of said waistband;

wherein said anterior portion of said crotch band has a posterior surface;

wherein said posterior surface of said anterior portion of said crotch band is absorbent so as to allow said garment to be used without said pouch, if so desired;

wherein said crotch band has a posterior portion; and wherein said posterior portion of said crotch band is replaceably attached to said posterior portion of said waistband, wherein said pouch is a sheet of material; and wherein said sheet of material has a pair of opposite edges, wherein said sheet of material is folded unto itself and said pair of opposite edges thereof are attached to each other by hook and loop fasteners so as to form a tube.

2. The garment as defined in claim 1, wherein said crotch band is for suspending between the legs of a user.

3. The garment as defined in claim 1, wherein said crotch band is flat; and wherein said crotch band is elongated.

4. The garment as defined in claim 1, wherein said pouch is replaceably attached to said posterior surface of said anterior portion of said crotch band.

5. The garment as defined in claim 1, wherein said tube is vertically-oriented and open ended for receiving the penis and holding the penis in an up position and a down position depending upon user preference.

6. The garment as defined in claim 1, wherein said tube has an exterior surface;

wherein said exterior surface of said tube has an anterior portion; and wherein said tube has an interior surface.

7. The garment as defined in claim 6, wherein said interior surface of said tube is lined with an absorbent material.

8. The garment as defined in claim 6, wherein said anterior portion of said exterior surface of said tube has hooks of hook and loop fasteners thereon; and wherein said hooks of said hook and loop fasteners cooperate with said posterior surface of said anterior portion of said crotch band which is not only of a material that is absorbent but is also of one that is cooperative with hooks of hook and loop fasteners.

9. The garment as defined in claim 1, wherein said means is snaps.

10. The garment as defined in claim 1, wherein said means is hook and loop fasteners.

\* \* \* \* \*